United States Patent
Hohlrieder et al.

(10) Patent No.: US 11,129,700 B2
(45) Date of Patent: Sep. 28, 2021

(54) MEDICAL ARRANGEMENT FOR SHUTTING OFF A BODY CHANNEL

(71) Applicant: A.M.I. Agency for Medical Innovations GmbH, Feldkirch (AT)

(72) Inventors: Martin Hohlrieder, Gotzis (AT); Marc Jablonowski, Lauterach (AT)

(73) Assignee: A.M.I. Agency for Medical Innovations GmbH, Feldkirch (AT)

(*) Notice: Subject to any disclaimer, the term of this patent is extended or adjusted under 35 U.S.C. 154(b) by 357 days.

(21) Appl. No.: 16/305,207

(22) PCT Filed: May 12, 2017

(86) PCT No.: PCT/AT2017/000036
§ 371 (c)(1),
(2) Date: Nov. 28, 2018

(87) PCT Pub. No.: WO2017/214643
PCT Pub. Date: Dec. 21, 2017

(65) Prior Publication Data
US 2020/0315764 A1     Oct. 8, 2020

(30) Foreign Application Priority Data
Jun. 14, 2016 (AT) .................... A 294/2016

(51) Int. Cl.
*A61F 2/00* (2006.01)
(52) U.S. Cl.
CPC ............ *A61F 2/004* (2013.01); *A61F 2/0027* (2013.01); *A61F 2230/0065* (2013.01); *A61F 2250/0013* (2013.01)
(58) Field of Classification Search
CPC .............. A61F 2/0027; A61F 2/004; A61F 2250/0013; A61F 2230/0065
See application file for complete search history.

(56) References Cited

U.S. PATENT DOCUMENTS

| 3,863,622 A | 2/1975 | Buuck |
| 4,222,377 A | 9/1980 | Burton |

(Continued)

FOREIGN PATENT DOCUMENTS

| CN | 101120895 | 2/2008 |
| CN | 101460218 | 6/2009 |

(Continued)

OTHER PUBLICATIONS

Artifical Urinary Sphincter, Wikipedia, 2 pages, downloaded on Apr. 19, 2016, https://en.wikipedia.org/wiki/Artificial_urinary_sphincter.

*Primary Examiner* — Christine H Matthews
*Assistant Examiner* — Joshua Daryl D Lannu
(74) *Attorney, Agent, or Firm* — Volpe Koenig

(57) ABSTRACT

A medical device for shutting off an anatomical channel is provided, including: a band section that can be placed around the body tissue surrounding the body channel and can be closed to form a ring enclosing a passage opening for the body tissue, and that includes a cavity which makes up one part of a receiving chamber of the arrangement, for receiving working fluid; and a pump unit for conveying the working fluid. The passage opening can be made smaller by introducing the working fluid into the cavity. An expansion body is provided having an expansion chamber, and the expansion body is arranged on the band section, on a side of the band section that faces the passage opening, and the expansion chamber can be made bigger by introducing an auxiliary fluid, which is separate from the working fluid, into the expansion chamber.

9 Claims, 4 Drawing Sheets

(56) References Cited

U.S. PATENT DOCUMENTS

| | | |
|---|---|---|
| 4,417,567 A | 11/1983 | Trick |
| 4,721,509 A | 1/1988 | Craggs |
| 4,784,660 A | 11/1988 | Fischell |
| 5,478,305 A | 12/1995 | Craggs |
| 5,976,109 A | 11/1999 | Heruth |
| 6,461,292 B1 | 10/2002 | Forsell |
| 6,470,892 B1 | 10/2002 | Forsell |
| 6,475,136 B1 | 11/2002 | Forsell |
| 7,172,607 B2 | 2/2007 | Hofle et al. |
| 7,217,237 B2 * | 5/2007 | Wassermann .......... A61F 2/004 600/29 |
| 8,870,742 B2 | 10/2014 | Dlugos, Jr. et al. |
| 10,139,304 B2 | 11/2018 | Lamraoui |
| 2003/0045775 A1 | 3/2003 | Forsell |
| 2003/0105385 A1 | 6/2003 | Forsell |
| 2004/0260319 A1 | 12/2004 | Egle |
| 2006/0183967 A1 * | 8/2006 | Lechner .................. A61F 5/003 600/37 |
| 2006/0211913 A1 | 9/2006 | Dlugos et al. |
| 2007/0156013 A1 | 7/2007 | Birh |
| 2009/0248109 A1 | 10/2009 | Forsell |
| 2010/0076254 A1 | 3/2010 | Jimenez et al. |
| 2010/0211175 A1 | 8/2010 | Gomez-Llorens |
| 2012/0123195 A1 | 5/2012 | Woodruff et al. |
| 2012/0130157 A1 | 5/2012 | Cotner et al. |
| 2012/0157759 A1 | 6/2012 | Wirbisky et al. |
| 2014/0364686 A1 * | 12/2014 | McClurg ................ A61F 2/004 600/31 |
| 2015/0359617 A1 | 12/2015 | Forsell |
| 2016/0089224 A1 | 3/2016 | Taylor |
| 2017/0252141 A1 | 9/2017 | Al Harmi et al. |

FOREIGN PATENT DOCUMENTS

| | | |
|---|---|---|
| CN | 105393100 | 3/2016 |
| DE | 9308196 | 12/1993 |
| DE | 10013519 | 10/2001 |
| DE | 202007004083 | 8/2007 |
| EP | 0348114 | 12/1989 |
| EP | 1389453 | 3/2007 |
| EP | 1484038 | 8/2007 |
| EP | 1832253 | 9/2007 |
| EP | 1992315 | 11/2008 |
| EP | 2123238 | 11/2009 |
| EP | 2400239 | 12/2011 |
| FR | 1291158 | 5/1961 |
| FR | 2373272 | 7/1978 |
| WO | 2009136121 | 11/2009 |
| WO | 2009136124 | 11/2009 |
| WO | 2017205883 | 12/2017 |
| WO | 2017214644 | 12/2017 |

* cited by examiner

MEDICAL ARRANGEMENT FOR SHUTTING OFF A BODY CHANNEL

BACKGROUND

The invention relates to a medical device for shutting off an anatomical channel, said device comprising a band part which can be placed around the body tissue surrounding the anatomical channel and which can be closed to form a ring that encloses a through-opening for the body tissue, which band part has a hollow chamber constituting a part of a receiving space of the device for receiving working fluid, and a pump unit which serves to convey the working fluid, wherein the through-opening can be made smaller by introducing the working fluid into the hollow chamber.

Medical devices for shutting off an anatomical channel are used, inter alia, as artificial (sphincter) muscles for aiding or replacing weakened natural muscles in the human or animal body. Examples of the uses of such devices are anal bands for closing an anus, possibly an artificial anus, and artificial sphincter muscles for closing the urethra in order to treat incontinence. Further areas of use are, for example, bands for closing a bile duct. The band part of such medical devices is also designated as a cuff, sleeve or artificial sphincter.

The hollow chamber of the band part can be emptied by the user when necessary in order to increase the cross-sectional area of the through-opening and to allow substances and/or liquids contained in the anatomical channel to pass through. For example, in the use as an artificial sphincter muscle for the urethra, there is often a subsequent automatic closure of the anatomical channel by reverse pumping of working fluid (optionally via a throttle valve) into the hollow chamber of the band part. In an artificial urinary sphincter of this kind for male patients, a pump for pumping working fluid is usually implanted in the scrotum. The pumping of working fluid out of the hollow chamber can then be effected by pressure exerted on a flexible part of the pump. The reverse pumping of working fluid into the hollow chamber can be effected by a resiliently elastic element of the pump. The through-opening of the medical device can often also be made smaller again by deliberate manipulation by the user, i.e. by manual actuation of the pump unit.

For example, US 2014/0364686 A1 discloses several illustrative embodiments of medical devices in the form of urethral sphincters which have a band part with two hollow chambers. A partition wall, which separates the two hollow chambers from each other, has a valve that permits an exchange of fluid between the hollow chambers. By the use of a pump, the fluid can be moved from one of the hollow chambers to the other hollow chamber in order to open the anatomical channel.

A problem with medical devices for narrowing or shutting off an anatomical channel is that they can cause erosion of the body tissue as a consequence of the pressure exerted on the body tissue by the device. Therefore, the pressure of the working fluid in the hollow chamber is generally chosen such that the erosion of body tissue can be kept to a minimum while, at the same time, reliable shutting-off of the anatomical channel is still achieved.

In the event of straining of the abdominal muscles, which occurs, in most cases involuntarily, for example when climbing stairs, lifting loads, sneezing, coughing or laughing, there is a brief increase in intra-abdominal pressure. The short-lived pressure peaks act in particular on the internal (hollow) organs arranged in the abdominal space, e.g. the bladder and intestines. The pressure in the (hollow) organs thus increases, which can lead to substances and/or liquid escaping through the portion of the anatomical channel shut off by the band part. This type of incontinence is also referred to as stress incontinence.

U.S. Pat. No. 5,478,305 A discloses a medical device which is of the type mentioned at the outset and which is used for treating urinary or fecal incontinence. The band part, referred to as a cuff in said document, is made of silicone. By filling the cuff with working fluid, the pressure in the hollow space of the cuff rises, and the resulting displacement of an inner portion of the cuff in the direction toward the longitudinal center axis closes the anatomical channel. A flexible balloon (stress balloon) made of silicone is arranged between two parts of a connection line which brings a pump into fluidic communication with the cuff. The hollow space of the stress balloon is filled with working fluid. A brief increase of the internal body pressure causes a decrease in volume of the hollow space of the stress balloon, as a result of which working fluid is forced into the cuff. By this brief increase in the pressure of the working fluid, the anatomical channel can also be kept shut off during a stress event, and leakage can be prevented. When the internal body pressure decreases again, the volume of the hollow space of the stress balloon increases and the pressure of the working fluid decreases, wherein working fluid flows out of the cuff. When the pressure of the working fluid in the cuff is increased in order to close the anatomical channel, the volume of the balloon also increases, such that a correspondingly large quantity of liquid has to be displaced by the pump.

SUMMARY

The object of the invention is to make available an advantageous device which is of the type mentioned at the outset and which can be used to treat stress incontinence.

According to the invention, this is achieved by a device having one or more features of the invention.

The device according to the invention has an expansion body with an expansion chamber, wherein the expansion body is arranged in the receiving space for the working fluid or is arranged at the band part, on a side of the band part directed toward the through-opening. The expansion chamber can be made larger by introducing an auxiliary fluid, separate from the working fluid, into the expansion chamber. The expansion chamber can thus be filled with the auxiliary fluid independently of the working fluid.

If a stress event occurs, e.g. caused by an increase of the internal body pressure during a coughing fit, the expansion chamber grows larger, as a result of which an additional force can be applied to the body tissue guided through the through-opening. The anatomical channel is thus also reliably shut off during a stress event. During a stress event, the internal body pressure (=ambient pressure) is at any rate above the atmospheric pressure.'

The auxiliary fluid is expediently completely separate from the working fluid, i.e. no exchange of fluid takes place between the auxiliary fluid and the working fluid.

Through the provision of two independent fluid systems, additional options are possible as regards the configuration of the medical device.

The increase in the volume of the expansion body by introduction of auxiliary fluid into the expansion chamber takes place in particular by stretching or unfolding of the expansion body.

Provision can be made that the expansion body is elastically extensible. In other embodiments, however, the expansion body can also be formed from an at least substantially non-extensible material. Thus, it would be possible to provide a bellows which is closed at both ends and which stretches out as auxiliary fluid is introduced into the expansion chamber. However, it is also conceivable and possible in principle that the change of volume of the expansion body is effected by displacement of at least one displaceable wall of the expansion body. The displaceable wall could be a piston, for example, which is movable by introducing auxiliary fluid into the expansion chamber.

In this document, the receiving space for the working fluid denotes the entire inner space of the device in which working fluid is located during operation of the device. In the case of the expansion body being arranged in the receiving space for the working fluid, the expansion body could be arranged, for example, in the hollow chamber of the band part or of a working fluid line that connects the hollow chamber to the pump unit. The expansion body is particularly preferably arranged in the pump unit.

The pump unit expediently has a pump part having an interior for receiving working fluid, the volume of which interior is variable by a drive. In the case of the expansion body being arranged in the pump unit, provision is expediently made that the expansion body is arranged in the interior of the pump p art.

By use of the pump unit, working fluid can be introduced into the hollow chamber of the band part. The anatomical channel can be shut off when an inner portion of the band part directed toward the through-opening is displaced in the direction toward a longitudinal center axis of the through-opening.

In the embodiment in which the expansion body is arranged in the receiving space for working fluid, the expansion body is thus surrounded by the working fluid during operation of the device. As the expansion chamber fills with auxiliary fluid, with the volume of the expansion chamber increasing as a result, the pressure of the working fluid increases, wherein the inner portion of the band part is displaced farther in the direction toward the longitudinal center axis of the through-opening. This leads to greater compression of the body tissue surrounding the anatomical channel.

In one embodiment according to the invention, in which the expansion body is arranged at the band part, on a side of the band part directed toward the through-opening, i.e. on the inner portion of the band part, the filling of the expansion chamber with auxiliary fluid causes an increase in the volume of the expansion chamber, which acts with a compressing effect directly on the body tissue surrounding the anatomical channel, so as to ensure that the anatomical channel is reliably shut off during a stress event.

The filling of the expansion chamber could in principle take place using a sensor-controlled auxiliary fluid pump, wherein a pressure increase within the body is detected by a pressure sensor, and the auxiliary fluid pump could be activated depending on this. In a preferred embodiment, however, the device has an auxiliary fluid container with a storage chamber for the auxiliary fluid, the volume of which storage chamber is variable depending on the ambient pressure. The auxiliary fluid container is connected to the expansion chamber via an auxiliary fluid line.

The auxiliary fluid container is advantageously implantable in the body, particularly in the abdominal space, wherein the internal body pressure prevailing within the body acts on the auxiliary fluid container. The pressure of the auxiliary fluid then expediently corresponds to the internal body pressure. When abdominal muscles strain during a stress event, the volume of the storage chamber of the auxiliary fluid container changes depending on the internal body pressure. Auxiliary fluid is ejected from the storage chamber and conveyed through the auxiliary fluid line into the expansion chamber. Therefore, no additional pump is needed to convey auxiliary fluid.

The auxiliary fluid container expediently has a flexible wall delimiting the storage chamber. In this context, flexible is considered to mean a bendable wall, but one that does not necessarily have to be extensible. On the contrary, the flexible wall is designed to be at least substantially non-extensible. During the filling of the auxiliary fluid container, there is therefore no material extension, i.e. the volume of the storage chamber can be increased only by unfolding of the flexible wall. The volume of the storage chamber is expediently limited to a maximum storage volume of the storage chamber.

In an advantageous embodiment, provision is made that the flexible wall delimiting the storage chamber is pliable. That is to say, the wall does not return to an earlier shape spontaneously (=without the action of an external force). In the case of a wall designed to be pliable, the auxiliary fluid container also be referred to as dimensionally unstable.

In another embodiment, the auxiliary fluid container could also be provided, for example, in the form of a bellows that is closed at both ends, wherein the volume of the storage chamber can be increased by extension of the bellows.

However, it would also be conceivable in principle that the auxiliary fluid container has at least one displaceable wall, e.g. in the manner of a piston.

Advantageously, provision is made that the volume of the expansion chamber is at least substantially equal to zero when a working fluid is at a higher pressure compared to the pressure of the auxiliary fluid. If the volume of the expansion chamber in the release state is substantially equal to zero or relatively low, no auxiliary fluid or only a little auxiliary fluid has to be conveyed from the expansion chamber to the storage chamber during the adjustment of the band part from the release state to the shut-off state. The quantity of working fluid to be displaced can thus be minimized. In the case of the medical device having an electrically operated pump device, energy consumption can thus be reduced.

BRIEF DESCRIPTION OF THE DRAWINGS

Further advantages and details of the invention are explained below with reference to the attached drawings, in which.

DETAILED DESCRIPTION

Figure 1:
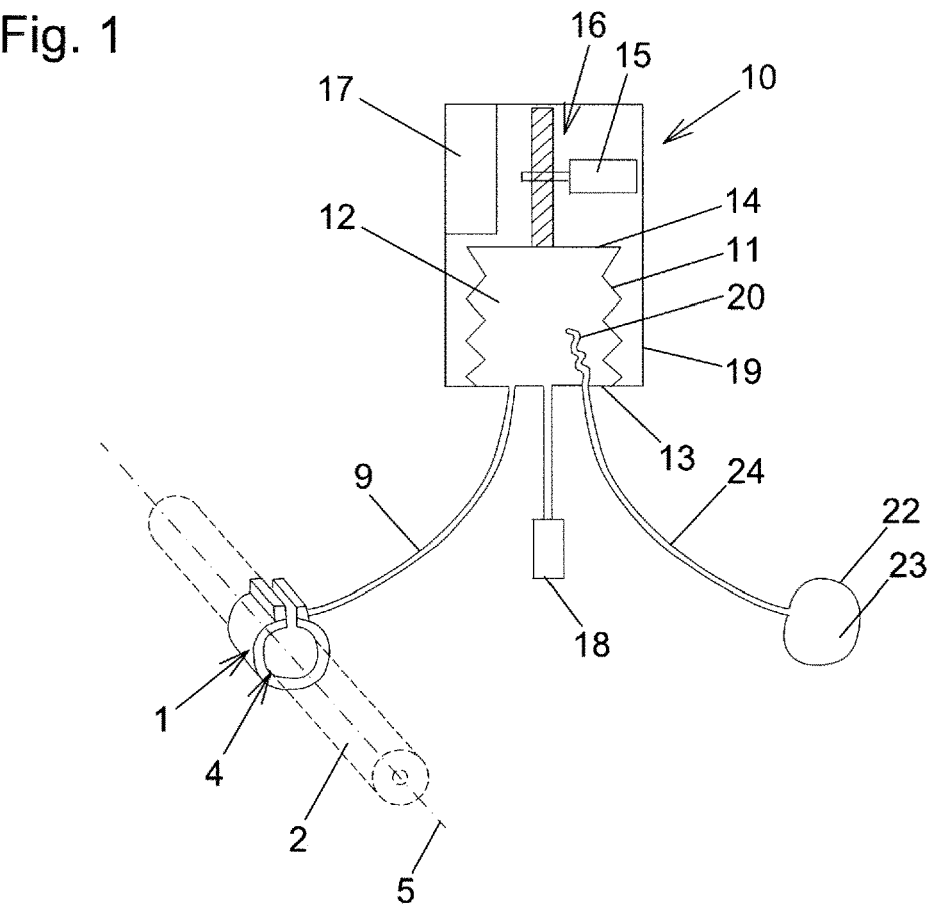
FIG. 1 shows a schematic view of a device configured as an artificial urethral sphincter, in a release state of the band part, in which state the ureter is opened.

A band part 1 of the medical device can be placed in a ring shape around the body tissue 2 surrounding the anatomical channel, here the urethra. The band part 1 has a hollow chamber 3 which extends in the direction of the longitudinal extent of the band part 1, in the illustrative embodiments substantially along the entire length of the band part 1. The band part 1 is thus configured like a hose, with ends closed at both sides.

A first and a second closure part 6, 7 are arranged at the two ends of the band part 1. The first closure part 6 has an insertion opening 6a into which a tongue 7a of the second closure part 7 can be inserted and locked therein.

Figure 5:
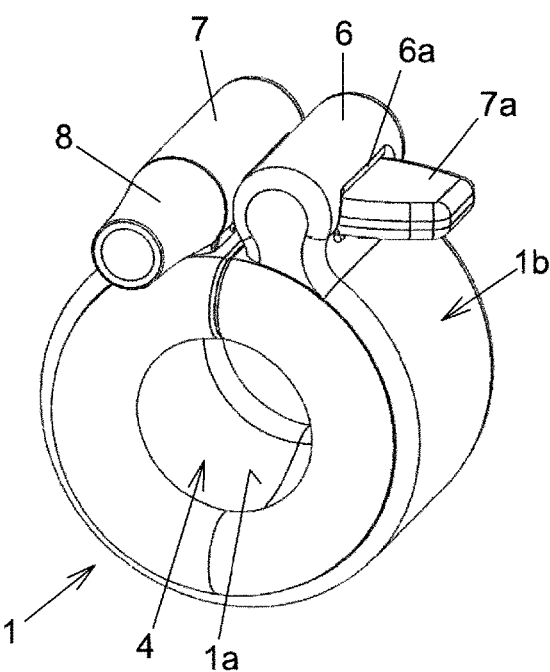

The closure parts 6, 7 thus form a closure with which the band part 1 can be closed to form a ring, in particular a circular ring (cf. FIG. 5). In the closed state, the band part 1 encloses a through-opening 4 for the body tissue 2 surrounding the anatomical channel.

A working fluid, in particular a liquid, e.g. saline solution, is located in the hollow chamber 3. The size of the through-opening 4 depends on the quantity of the working fluid in the hollow chamber 3. The through-opening 4 can be made smaller by introducing working fluid into the hollow chamber 3. A flexible inner portion 1a of the band part 1, which portion is adjacent to the longitudinal center axis 5 of the through-opening 4, is displaced in the direction toward the longitudinal center axis 5, as is known. By removing working fluid from the hollow chamber 3, the through-opening 4 can be made larger again.

Figure 6:
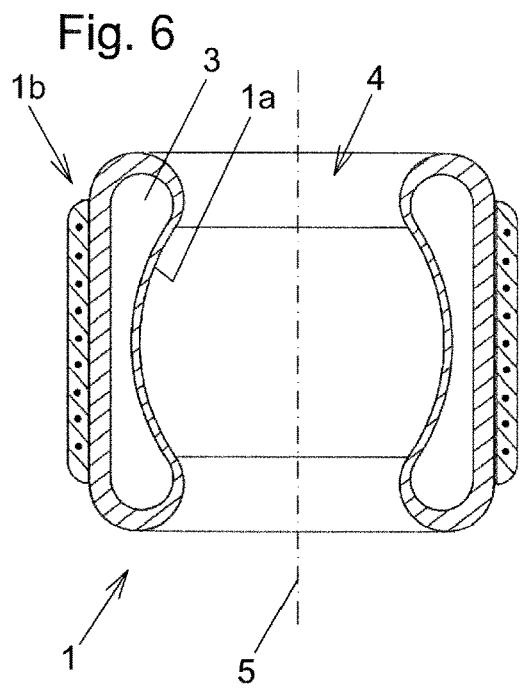
FIG. 6 shows a longitudinal center section (parallel to the longitudinal center axis of the through-opening and extending through the latter) through the band part in the state according to FIG. 5.
Figure 7:
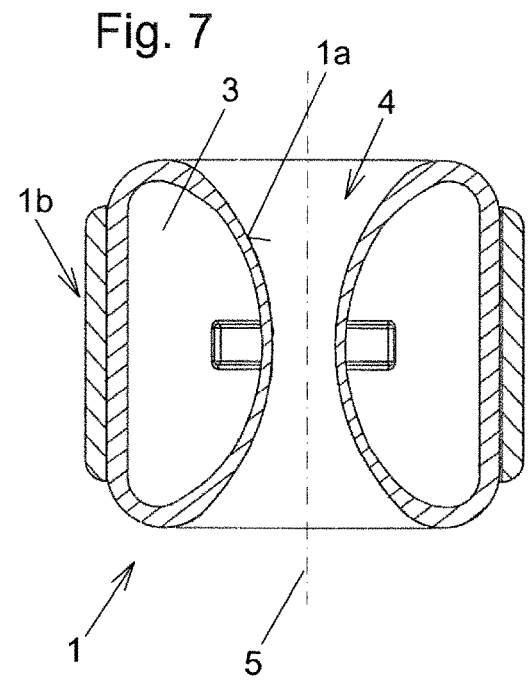
FIG. 7 shows a longitudinal center section analogous to FIG. 6, but in the shut-off state of the band part.

FIG. 6 shows the state in which the through-opening 4 is at its largest (wherein the pressure of the working fluid in the hollow chamber 3 corresponds to the ambient pressure). FIG. 7 shows a state in which it is filled with the working fluid, in particular the state in which it is filled to the maximum with working fluid (wherein the pressure of the working fluid in the hollow chamber 3 is above the ambient pressure). The formation of folds, which would occur in particular if the band part is not placed around the ureter, is not shown in FIG. 7. By contrast, a rear portion 1b of the band part 1, set back from the longitudinal center axis 5, can be made stiff in relation to the inner portion 1a, in particular by a reinforcing layer, as a result of which a deformation of the rear portion 1b can be at least largely avoided.

Figure 2:
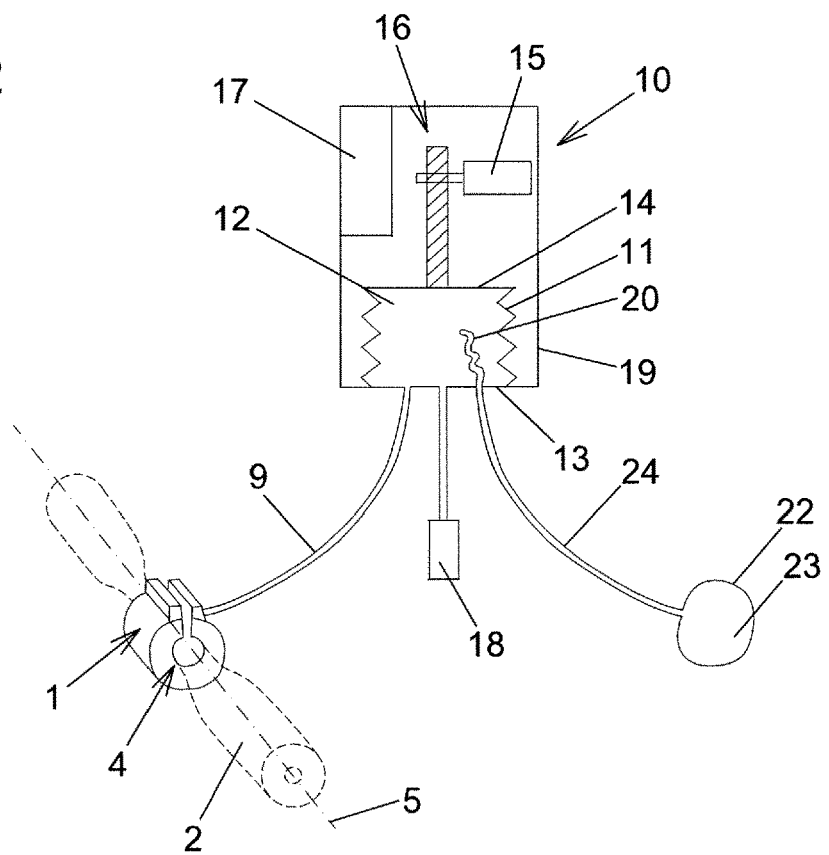
FIG. 2 shows a view analogous to FIG. 1, in a shut-off state of the band part, in which state the ureter is closed.

In the closed state of the band part 1 placed around the anatomical channel, said band part 1 can thus adopt a release state, in which the anatomical channel is opened (cf. FIG. 1), and a shut-off state, in which the anatomical channel is closed (cf. FIG. 2). In the release state, the pressure of the working fluid in the hollow chamber 3 can for example correspond to the atmospheric pressure. In the shut-off state, the hollow chamber 3 is filled with such a quantity of working fluid that the anatomical channel is closed.

Various modifications of the design of the band part are conceivable and possible. For example, it would be possible for special closure parts mounted on the band part 1 to be omitted altogether and for the two ends of the band part to be sewn to each other.

The band part 1 can be made from silicone in a known manner. Other biocompatible materials may also be used in principle.

In the illustrative embodiment, an attachment stub 8 is integrally formed on one of the closure parts, the interior of which attachment stub 8 is connected to the hollow chamber 3 via a channel running through the closure part 7. Such an attachment stub could also be provided at another location of the band part. A working fluid line 9 configured as a hose is attached at the attachment stub 8.

Figure 3:
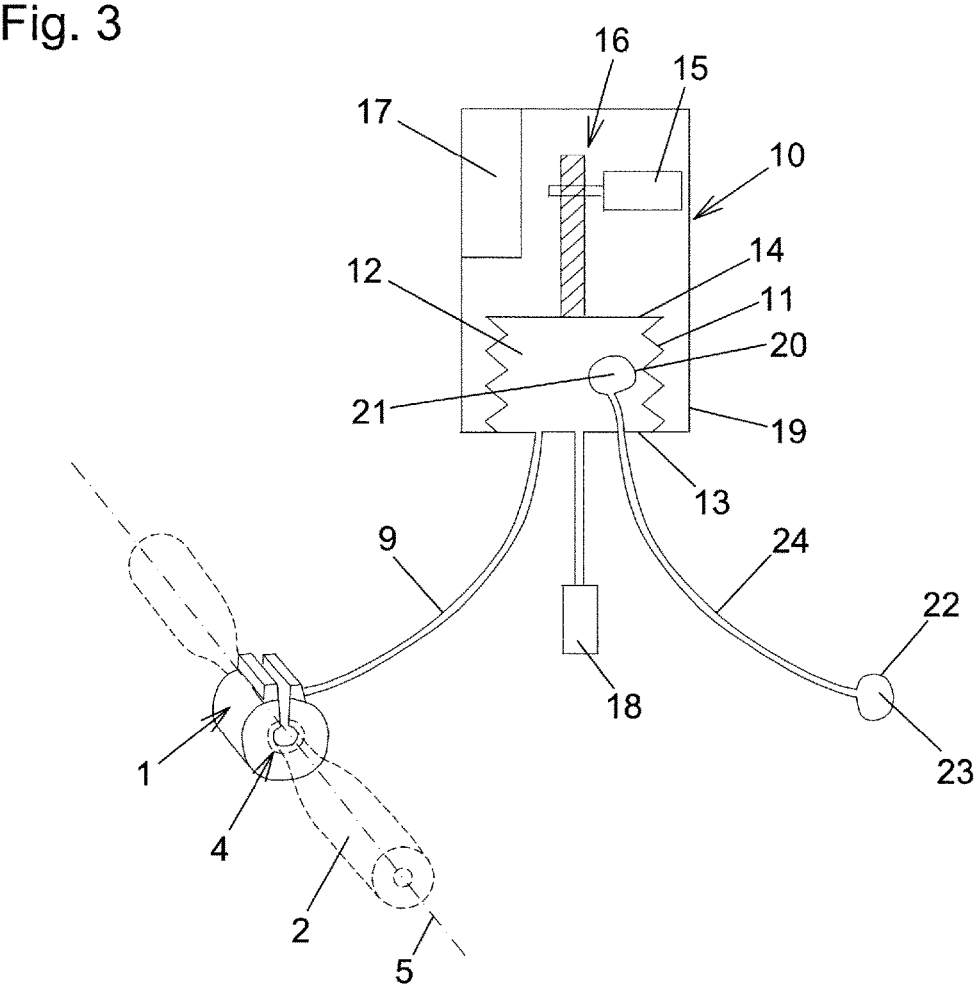
FIG. 3 shows a view analogous to FIG. 1, in a stress state of the band part, in which state an additional force is exerted on the ureter.
Figure 4:
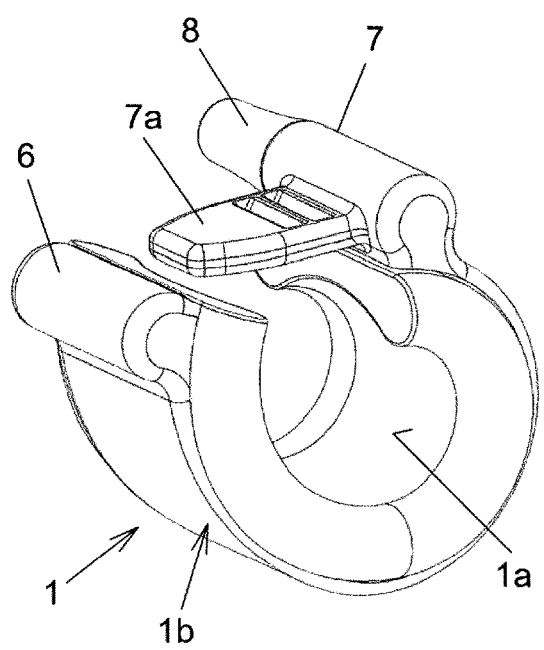
FIGS. 4 and 5 show oblique views of the free, i.e. not implanted, band part of the device in an opened state and a closed state, specifically corresponding to the release state.

The band part 1 is connected via the channel of the working fluid line 9 to a pump part 11 of a pump unit 10, which is spatially separate from the band part 1 (cf. FIGS. 1 to 3). By the use of the pump unit 10, the quantity of working fluid in the hollow chamber 3 of the band part 1 can be changed.

A receiving space for receiving the working fluid (=working fluid receiving space) of the medical device comprises the entire continuous inner space of the device in which working fluid is located during operation. The hollow chamber 3 of the band part 1, the channel of the closure part of the band part 1 extending through the closure part, and the channel of the working fluid line thus each form a part of the receiving space for the working fluid. In the illustrative embodiment, the pump part 11 of the pump unit 10 has an interior 12 which is filled with working fluid and which likewise forms a part of the receiving space of the device.

To fill the receiving space of the medical device with working fluid, a port 18 is present in the customary way. This port 18 can be attached to the pump part 11 via a hose, for example.

In the illustrative embodiments, the pump part 11 is formed by a bellows which is closed by a bottom part 13 and a cover part, the latter constituting an actuating element 14. An electric drive 15 acts on the actuating element 14 via a gear 16, for example a worm gear, in order to change the volume of the interior 12. The gear 16 is expediently self-locking, such that an adopted position of the actuating element 14 is maintained without supply of electrical energy to the drive 15.

In the illustrative embodiment, the pump part 11 thus forms at the same time a reservoir for the working fluid with which the hollow chamber 3 of the band part 1 is filled in order to close the anatomical channel. For example, the pump part 11 could also be formed by a piston-cylinder unit, in which case the actuating element 14 would be formed by the piston of this piston-cylinder unit.

The electric drive 15 is controlled by a control electronics unit 17 of the pump unit 10, which also has a battery (not shown) for supplying electric current to the drive 15. The control electronics unit 17 is operated by the user via a suitable user interface (not shown). The user interface can be an operating unit that is linked to the control electronics unit 17 by wire or by radio and that has corresponding switches.

The user interface can be arranged outside the body. Implantation of the user interface is conceivable and possible. A separate user interface could in principle also be omitted, in which case at least one operating element activatable by the user would be arranged at the pump unit 10. This would accordingly have to be able to be activated from outside the body.

The components of the pump unit 10 are arranged in a housing 19. The housing 19 is made of a biocompatible material or is encased by such a material.

The medical device moreover has an auxiliary fluid container 22 with a storage chamber 23 filled with auxiliary fluid during operation of the device. The auxiliary fluid container 22 is expediently implanted in the body. The auxiliary fluid container 22 has a flexible wall delimiting the storage chamber 23. This flexible wall can be designed to be at least substantially non-extensible.

"Substantially non-extensible" denotes the material property of the wall of the auxiliary fluid container 22 whereby, starting from a state of maximum deployment, the volume of the storage chamber 23 increases by less than 10%, preferably by less than 5%, when the pressure of the auxiliary fluid in the auxiliary fluid container 22 increases by 0.1 bar. The auxiliary fluid container 22 could have a reinforcement, which expediently has an elastic modulus of at least 1,000 N/mm$^2$, preferably of at least 5,000 N/mm$^2$.

In the illustrative embodiment, the wall of the auxiliary fluid container 22 is also designed to be pliable, i.e. the wall does not return spontaneously to an earlier shape. The wall of the auxiliary fluid container 22 could in this case be formed, for example, of a plastic film. According to the illustrative embodiments shown, the auxiliary fluid container 22 can therefore expediently fold up, wherein the volume of the storage chamber 23 can be varied by folding up or folding out of the auxiliary fluid container 22, depending on an ambient pressure (=internal body pressure).

The pressure of the auxiliary fluid expediently corresponds to the ambient pressure (=internal body pressure) during operation of the device.

The wall of the auxiliary fluid container 22 is expediently made of a biocompatible material, e.g. polyamide or silicone, or is encased by such a material. The optional reinforcement can be embedded in this material.

The storage chamber 23 of the auxiliary fluid container 22 is fluidically connected by an auxiliary fluid line 24 to an expansion chamber 21 of an expansion body 20. The storage chamber 23, the inner channel of the auxiliary fluid line 24 and the expansion chamber 21 each form a part of an auxiliary fluid receiving space of the medical device. The auxiliary fluid receiving space signifies the entire inner space of the device in which auxiliary fluid is located during operation of the device.

The auxiliary fluid, separate from the working fluid, could be introduced into the auxiliary fluid line 24 via a port (not shown in detail) or directly into the storage chamber 23. The auxiliary fluid is expediently a liquid, e.g. saline solution.

In the first illustrative embodiment, the expansion body 20 is arranged in the receiving space of the device filled with working fluid, namely in the interior 12 of the pump part 11.

The volume of the expansion chamber 21 can be increased by introduction of auxiliary fluid into the expansion chamber 21 by unfolding or stretching of the expansion body 20. If the increase in volume is effected purely by unfolding, the expansion body 20 can be made of a non-extensible material, such that the maximum volume of the expansion chamber 21 is limited. Therefore, an increase in the pressure of the working fluid (as explained further below) is limited by the limitation of the volume of the expansion chamber 21. However, the volume of the expansion chamber 21 can be increased by an elastically extensible design of the expansion body 20.

The expansion body 20 can also be designed to be pliable, i.e. the expansion body 21 is then dimensionally unstable, as is indicated in FIGS. 1 and 2.

At least in the shut-off state of the band part 1 shown in FIG. 2, the auxiliary fluid is at a lower pressure than the working fluid. The expansion chamber 21 of the expansion body 20 is preferably folded up completely. Therefore, there is at least substantially no auxiliary fluid present in the expansion chamber 21. In other words, the auxiliary fluid is thus forced out of the expansion chamber 21 into the storage chamber 23 of the auxiliary fluid container 22 on account of the higher pressure of the working fluid acting on the expansion body 20. The volume of the expansion chamber 21 is therefore at least substantially equal to zero. In a modified embodiment, this could in principle also be otherwise.

In FIG. 1, which relates to the release state of the band part 1, the expansion chamber 21 is shown folded up completely, i.e. with a volume substantially equal to zero. This is the case if the auxiliary fluid is at a lower pressure than the working fluid and/or if the auxiliary fluid is forced out of the expansion chamber 21 by the elasticity of the expansion body 20 when there is equality of the pressure (of the auxiliary fluid and of the working fluid). A certain residual volume of the expansion chamber 21 may also be present in the release state.

If the pressure within the body (=internal body pressure) rises, for example during a coughing fit, a force brought about by the internal body pressure acts directly on the auxiliary fluid container 22. When a force acts on the auxiliary fluid container 22, the pressure of the auxiliary fluid increases correspondingly. If the internal body pressure, and therefore the pressure of the auxiliary fluid, is greater than the pressure of the working fluid, the auxiliary fluid container 22 is compressed and auxiliary fluid is forced out of the storage chamber 23 into the expansion chamber 21. If the expansion body 20 sets an elastic restoring force counter to the expansion of the expansion chamber 21, this elastic restoring force can also be overcome by the pressure of the auxiliary fluid (the expansion body 20 is thus expanded only when the ambient pressure exceeds the pressure of the working fluid to such an extent that the elastic restoring force is also overcome by the pressure of the auxiliary fluid). The resulting increase of the volume of the expansion chamber 21 leads to an increase of the pressure in the interior 12 of the pump part 11. Working fluid is ejected from the interior 12 and introduced into the hollow chamber 3 of the band part 1. The inner portion 1a of the band part 1 is displaced in the direction toward the longitudinal center axis 5, and an additional force is applied to the body tissue 2 guided through the through-opening 4. This state of the band part 1 is referred to in this document as the stress state and is shown in FIG. 3.

As the internal body pressure, and therefore the pressure of the auxiliary fluid, subsequently decreases again such that the pressure of the auxiliary fluid is less than the pressure of the working fluid (if appropriate plus the elastic restoring force of the expansion body), the volume of the storage chamber 23 of the auxiliary fluid container 22 increases as it receives auxiliary fluid discharged from the expansion chamber 21 of the expansion body 20. After the stress event, the band part 1 is thus once again located in the shut-off state (cf. FIG. 2).

When the anatomical channel is to be opened from the shut-off state of the band part 1, e.g. to pass urine, i.e. when the band part 1 adopts the release state (see FIG. 1) by displacement of working fluid from the hollow chamber 3 into the interior 12 of the pump part 11, and when there is also no stress event, the volume of the expansion chamber 21 remains substantially equal to zero or relatively slight. Therefore, during the adjustment of the band part 1 from the shut-off state to the release state, and vice versa, no auxiliary fluid or only a little auxiliary fluid has to be conveyed from the expansion chamber 21 into the storage chamber 23 of the auxiliary fluid container 22. The quantity of working fluid to be displaced can thus be minimized, and the associated energy consumption for displacement of working fluid can be reduced. The interval for charging or replacing the battery of the control electronics unit 17 can thus be lengthened.

Figure 8:
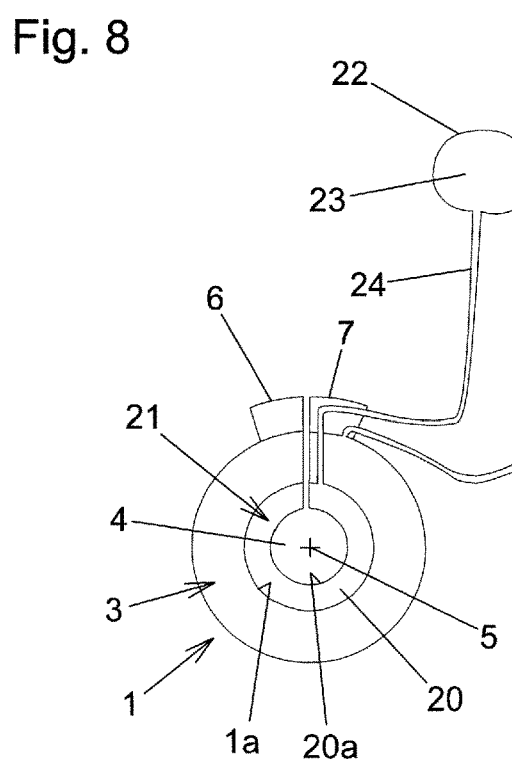
FIG. 8 shows a schematic view of a second embodiment of an artificial urethral sphincter, in a shut-off state of the band part, in which state the ureter is closed.
Figure 9:
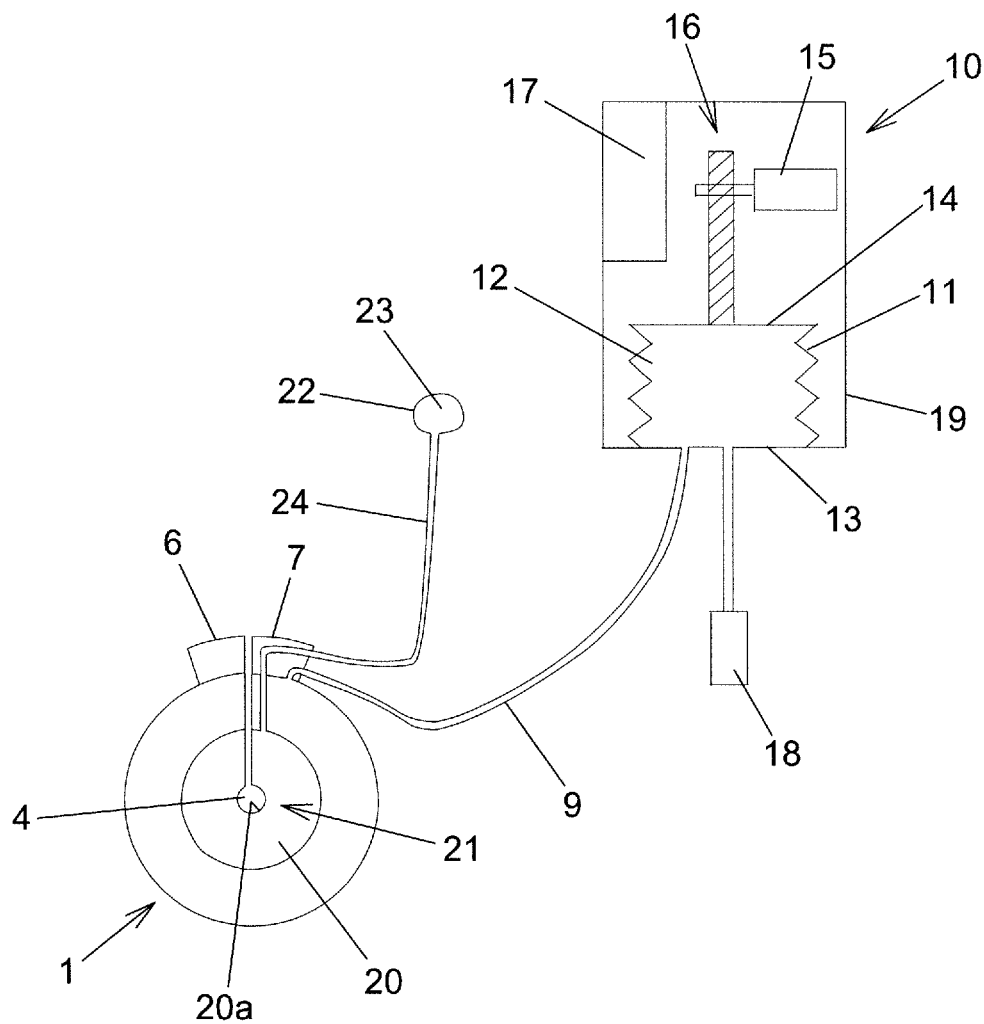
FIG. 9 shows a view analogous to FIG. 8 in a stress state of the band part, in which state an additional force is exerted on the ureter.

FIGS. 8 and 9 show a second illustrative embodiment of a medical device according to the invention. The structure of the pump unit 10 and of the auxiliary fluid container 22 corresponds to that of the first illustrative embodiment, and therefore the explanations concerning the second illustrative embodiment focus mainly on the differences in relation to the first illustrative embodiment. Apart from the differences set out below, the explanations concerning the first illustrative embodiment also apply to the second illustrative embodiment. Thus, in terms of the configuration of the closure parts 6, 7 of the band part 1, which are shown only schematically in FIGS. 8 and 9, reference is also made to the explanations concerning the first illustrative embodiment.

In the medical device according to the second illustrative embodiment, provision is made that the expansion body 20 is arranged at the band part 1, on a side of the band part 1 directed toward the through-opening 4, i.e. on the inner portion 1a. This is shown schematically in FIGS. 8 and 9, wherein the expansion chamber 21 extends in the direction of the longitudinal extent of the band part 1, substantially along the entire length of the band part 1. Therefore, in the second illustrative embodiment, the expansion body 20 is configured as a hose closed at both ends.

In the closed state of the band part 1, the expansion body 20 arranged at the band part 1 has, in relation to the circumferential direction of the longitudinal center axis 5, a substantially encircling bearing surface 20a for bearing on the body tissue 2.

In the shut-off state of the closed band part 1, the hollow chamber 3 is filled with such a quantity of working fluid that the anatomical channel is closed (cf. FIG. 8).

When working fluid is drained off, the band part 1 adopts the release state (not shown) in which the anatomical channel is opened.

If, starting from the shut-off state of the band part 1 shown in FIG. 8, the pressure within the body (=internal body pressure) increases in the presence of a stress event, this internal body pressure acts on the auxiliary fluid container 22, analogously to the first illustrative embodiment. If the internal body pressure, and therefore the pressure of the auxiliary fluid, is greater than the counter-pressure applied by the body tissue 2 to the expansion body 20, the auxiliary fluid container 22 is compressed and auxiliary fluid is conveyed out of the storage chamber 23 into the expansion chamber 21 of the expansion body 20. If the expansion body 20 sets an elastic restoring force counter to the expansion of the expansion chamber 21, this elastic restoring force can also be overcome by the pressure of the auxiliary fluid. As a result of the increase in the volume of the expansion chamber 21, the expansion body 20 acts with a compressing effect directly on the body tissue 2 surrounding the anatomical channel, in order to ensure reliable shutting-off of the anatomical channel during a stress event (cf. the stress state of the band part 1 shown in FIG. 9, in which state an additional force is applied to the body tissue 2 guided through the through-opening 4). The body tissue 2 itself is not indicated in FIGS. 8 and 9.

When the internal body pressure again reaches a basic state, i.e. without a stress event being present, the auxiliary fluid flows back out of the expansion chamber 21 into the auxiliary fluid container 22 (cf. the shut-off state of the band part 1 shown in FIG. 8).

In the second illustrative embodiment, the reverse flow of the auxiliary fluid into the auxiliary fluid container 22 is thus effected by the counter-pressure exerted by the body tissue 2, together with the pressure exerted on the expansion body 20 by the hollow chamber 3 filled with working fluid. If the expansion body 20 sets an elastic restoring force counter to the expansion of the expansion chamber 21, this elastic restoring force can have a supporting effect in the reverse flow of the auxiliary fluid.

In the second illustrative embodiment, provision can be made that the expansion body 20 and the band part 1 are formed materially in one piece. Provision is expediently made that the expansion body 20 in the second illustrative embodiment is designed to be elastically extensible. In another embodiment, however, provision could also be made that the expansion body 20 is designed to be substantially non-extensible and/or pliable.

In the second illustrative embodiment, the band part 1 and/or the expansion body 20 could be made of a biocompatible material, e.g. silicone.

In the second illustrative embodiment, an attachment stub (not shown in detail) for connecting the band part 1 to the auxiliary fluid line 24 is integrally formed on the closure part 7. The interior of the attachment stub is connected to the expansion chamber 21 via a channel running through the closure part 7. Such an attachment stub could also be provided at another location of the expansion body 20 or of the band part 1.

Figure 10:
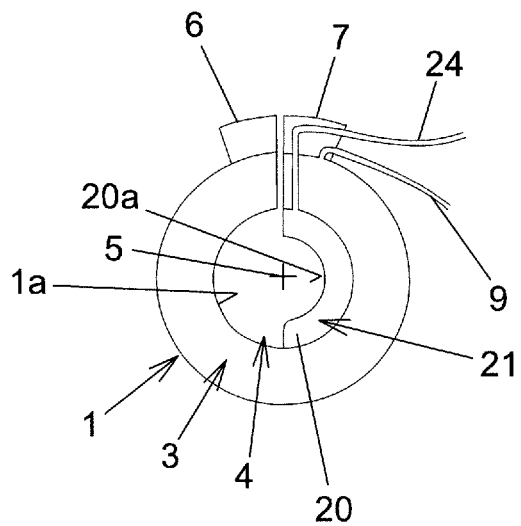
FIG. 10 show a schematic view of a variant of the band part according to the second embodiment, in a shut-off state of the band part, in which state the ureter is closed.
Figure 11:
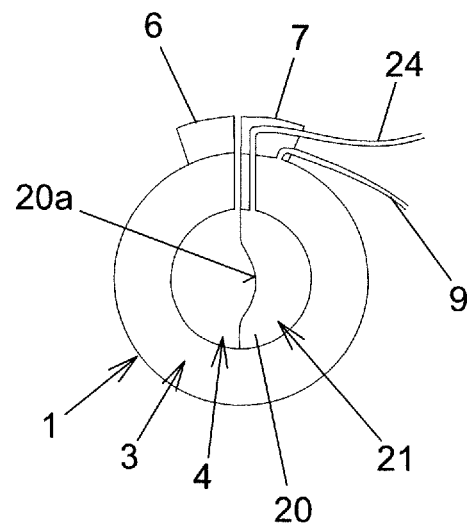
FIG. 11 shows a view, analogous to FIG. 10, in a stress state of the band part, in which state an additional force is exerted on the ureter.

FIGS. 10 and 11 show a variant of the band part 1 according to the second illustrative embodiment, wherein the differences in relation to the band part 1 shown in FIGS. 8 and 9 are discussed in particular below.

In the modified form of the band part 1 shown in FIGS. 10 and 11, the expansion body 20 extends in the direction of the longitudinal extent of the band part 1 over about half the length of the band part 1. In the shut-off state of the band part 1 shown in FIG. 10, the through-opening 4 is not circular, in contrast to the second illustrative embodiment. In the closed state of the band part 1, the bearing surface 20a of the expansion body 20 extends over 180° of the circumference of the through-opening 4 with respect to a circumferential direction starting from the longitudinal center axis 5.

In other respects, the band part 1 according to the modification shown in FIGS. 10 and 11 behaves analogously to the band part 1 of the second illustrative embodiment of the medical device when a stress event occurs, which is why reference is made to the relevant explanations concerning the second illustrative embodiment.

Besides the pump unit shown in the illustrative embodiments, the medical device could in principle also be used in combination with a pump unit that is commonly known from the prior art and that can be actuated manually, for example.

KEY TO THE REFERENCE NUMBERS 1 band part
1a inner portion
1b rear portion
2 body tissue
3 hollow chamber 4 through-opening
5 longitudinal center axis
6 first closure part
6a insertion opening
7 second closure part
7a tongue
8 attachment stub
9 working fluid line
10 pump unit
11 pump part
12 interior
13 bottom part
14 actuating element
15 drive
16 gear
17 control electronics unit
18 port
19 housing
20 expansion body
20a bearing surface
21 expansion chamber
22 auxiliary fluid container
23 storage chamber
24 auxiliary fluid line

The invention claimed is:

1. A medical device for shutting off an anatomical channel, comprising:
- a band part that is adapted to be placed around body tissue surrounding the anatomical channel and is adapted to be closed to form a ring that encloses a through-opening for the body tissue, and further includes a hollow chamber that forms part of a receiving space that is adapted to receive working fluid;
- a pump unit that is adapted to convey the working fluid to the hollow chamber such that the through-opening is adapted to be made smaller by introduction of the working fluid into the hollow chamber; and
- an expansion body with an expansion chamber, the expansion body being arranged at the band part, on a side of the band part directed toward the through-opening, and the expansion chamber being adapted to be made larger by introduction of an auxiliary fluid, separate from the working fluid, into the expansion chamber such that an expansion of the expansion chamber is independent of a filling state of the hollow chamber with the working fluid.

2. The medical device as claimed in claim 1, further comprising an auxiliary fluid container with a storage chamber for the auxiliary fluid, a volume of said storage chamber being variable depending on an ambient pressure, and the auxiliary fluid container being connected to the expansion chamber via an auxiliary fluid line.

3. The medical device as claimed in claim 2, wherein the auxiliary fluid container has a flexible wall delimiting the storage chamber.

4. The medical device as claimed in claim 3, wherein the wall is substantially non-extensible.

5. The medical device as claimed in claim 3, wherein the wall is pliable.

6. The medical device as claimed in claim 2, wherein a pressure of the auxiliary fluid is adapted to rise when a force is exerted on the auxiliary fluid container.

7. The medical device as claimed in claim 1, wherein the pump unit comprises a pump part which has an interior that is adapted to receive the working fluid, and a drive that is adapted to vary a volume of the interior.

8. The medical device as claimed in claim 1, wherein the expansion body arranged at the band part has a bearing surface that is adapted to bear on the body tissue.

9. The medical device as claimed in claim 1, wherein a volume of the expansion chamber is at least substantially equal to zero when the working fluid is at a higher pressure compared to a pressure of the auxiliary fluid.

* * * * *